United States Patent
Matsumoto et al.

[11] Patent Number: 6,126,706
[45] Date of Patent: Oct. 3, 2000

[54] METHOD OF CLEANING AND DISINFECTING CONTACT LENS

[75] Inventors: Satoru Matsumoto, Nagoya; Atsuko Sugiura, Yokkaichi, both of Japan

[73] Assignee: Tomey Corporation, Japan

[21] Appl. No.: 09/187,133

[22] Filed: Nov. 6, 1998

[30] Foreign Application Priority Data

Nov. 10, 1997 [JP] Japan ................................. 9-306744

[51] Int. Cl.[7] ............................... B08B 1/02; C11D 3/37; C11D 3/26
[52] U.S. Cl. ........................... 51/134; 510/112; 510/115; 510/475; 510/476; 510/477; 510/480; 510/506; 422/30; 422/37
[58] Field of Search ..................... 510/112, 115, 510/475, 477, 476, 480, 506; 422/37, 30; 134/42

[56] References Cited

U.S. PATENT DOCUMENTS

| | | | |
|---|---|---|---|
| 5,603,897 | 2/1997 | Heiler et al. | 422/30 |
| 5,925,317 | 7/1999 | Rogalskyj et al. | 422/30 |

FOREIGN PATENT DOCUMENTS 0915151  5/1999  European Pat. Off. .

*Primary Examiner*—Kery Fries
*Attorney, Agent, or Firm*—Wall Marjama Bilinski & Burr

[57] ABSTRACT

A method of cleaning and disinfecting a contact lens, comprising the steps of: preparing a disinfectant which is an aqueous solution containing an iodine-complex polymer, and a diluent which is an aqueous solution containing ethylenediamine tetraacetic acid and/or soluble salts thereof, and a nonionic surface active agent; mixing the disinfectant and the diluent to provide a mixed solution, such that an available iodine concentration of the mixed solution immediately after mixing is in a range of 0.01–50 ppm, and such that concentrations of the ethylenediamine tetraacetic acid and/or the soluble salts thereof, and the nonionic surface active agent in the mixed solution are in a range of 0.0001–1.0 w/v % and in a range of 0.01–1.0 w/v %, respectively; and immersing the contact lens in the mixed solution for cleaning and disinfecting the contact lens, resulting in gradual reduction of the available iodine remaining in the mixed solution, by the ethylenediamine tetraacetic acid and/or the soluble salts thereof.

9 Claims, No Drawings

METHOD OF CLEANING AND DISINFECTING CONTACT LENS

The present application is based on Japanese Patent Application No. 9-306744 filed Nov. 10, 1997, the content of which is incorporated hereinto by reference.

BACKGROUND OF THE INVENTION

1. Field of the Art

The present invention relates to a method of cleaning and disinfecting a contact lens by using an iodine-associated or iodine-complex polymer as an iodine germicide or disinfectant. In particular, the invention is concerned with such a method which permits effective cleaning and disinfection of the contact lens while assuring a high degree of safety of the eyes of the user.

2. Discussion of the Related Art

Generally, contact lenses are classified into non-water-absorbable or non-water-content contact lenses and water-absorbable or water-content contact lenses, or hard contact lenses and soft contact lenses. These contact lenses may be soiled with deposits such as protein lipid during wearing of the contact lenses on the eyes, which deposits derive from tear and lipid of the eyes. These deposits adhering to the contact lenses deteriorate the wearing comfort of the contact lenses as felt by the lens wearer, lower the eye sight of the lens wearer, and cause various troubles with the eyes such as hyperemia of the conjunctiva. In view of those problems, it is required to regularly clean the contact lenses by using a cleaning agent which contains a surface active agent and a protease, for instance, so as to remove the deposits for safe and comfortable wearing of the contact lenses.

When the contact lenses are continuously worn on the eyes, bacteria tend to adhere to and proliferate on the surfaces of the contact lenses, especially the surfaces of the water-content contact lenses. In view of this, it is required to disinfect the contact lenses every day for preventing the eyes of the lens wearer from being infected with the bacteria. Although the non-water-content contact lenses are not necessarily required to be disinfected as frequently as the water-content contact lenses, the non-water-content contact lenses are stored in a storing liquid which contains a germicide, so as to prevent proliferation of microorganisms during storage of the contact lenses which have been removed from the eyes.

Generally, the contact lens is cleaned and disinfected in different steps. However, it would be more convenient to the contact lens user if the contact lens can be cleaned and disinfected simultaneously in a single step. In view of this, there are proposed various methods of simultaneously cleaning and disinfecting the contact lens.

For disinfecting the contact lens, there have been practiced a thermal disinfecting method in which the contact lens is heated for disinfection by using a suitable apparatus for boiling the contact lens, and a chemical disinfecting method in which the contact lens is disinfected by a chemical disinfectant. As one example of the chemical disinfecting method, a technique which uses an iodine disinfectant or germicide has been attracting a great attention. The iodine disinfectant or germicide exhibits excellent antimicrobial activity and safety to the eyes of the user. The method using the iodine disinfectant or germicide, however, suffers from various drawbacks which result from the use of the iodine as described below. Accordingly, the iodine disinfectant or germicide is not capable of exhibiting its excellent disinfecting effect to a maximum extent while cleaning the contact lens.

For disinfecting the contact lens, the chemical disinfecting method is recently employed more often than the thermal disinfecting method since the chemical disinfecting method does not use the boiling apparatus as required in the thermal disinfecting method, and assures a simplified disinfecting procedure, so that the contact lens is disinfected at a relatively low cost. In the above-described chemical disinfecting method which uses the iodine disinfectant, the iodine is easily uptaked in the contact lens, whereby the contact lens is colored in amber or reddish purple peculiar to the color of the iodine after a relatively long period of contact of the contact lens with the iodine disinfectant. To avoid this, when the contact lens is disinfected by using the iodine disinfectant, the iodine contained in the disinfectant needs to be reduced by a suitable reducing agent immediately after the disinfection of the contact lens is completed. According to this arrangement, the disinfectant in which the iodine has been reduced is colorless and transparent, so that the disinfected contact lens is protected from being colored by the iodine.

JP-A-9-111298 discloses a composition for a contact lens, which is a combination of a first agent including an iodine germicide and a protease, and a second agent including a sulfur-containing reducing agent and a foaming agent. The second agent is covered with a coating layer for retarding the emission of the sulfur-containing reducing agent in a manner as described below. The disclosed composition includes a nonionic surface active agent in at least one of the first and second agents. The above-identified publication discloses that a soft contact lens is immersed in a treating solution of the first and second agents, so that the soft contact lens is cleaned and disinfected by the first agent. Thereafter, the coating layer of the second agent is dissolved, whereby the sulfur-containing reducing agent included in the second agent is dissolved in the treating solution. Accordingly, the iodine molecules remaining in the treating solution are reduced by the sulfur-containing reducing agent, so that the contact lens and the solution which have been colored in yellow or amber due to the iodine are made colorless.

The composition disclosed in the above publication includes an excessively large amount of the iodine germicide in an attempt to provide a sufficiently high disinfecting effect, and also includes the sulfur-containing reducing agent to reduce the excessive iodine germicide. The use of the sulfur-containing reducing agent inevitably pushes up the cost of manufacture of the composition, and causes a problem that the sulfur contained in the reducing agent may be released, undesirably precipitating in the treating solution. The inclusion of the excessive amount of the iodine in the treating solution increases the effective or available iodine concentration of the solution. In this case, the treating solution may exhibit a high degree of disinfecting effect. However, the contact lens tends to be damaged due to the excessively high available iodine concentration. Further, iodide ions which have been produced by neutralization of the iodine molecules are oxidized back into the iodine. In this case, the contact lens may be colored by the iodine, and the iodine may give rise to a problem of insufficient safety.

SUMMARY OF THE INVENTION

It is therefore an object of the present invention to provide a method of cleaning and disinfecting a contact lens by using an iodine disinfectant, wherein the contact lens can be sufficiently disinfected without suffering from adverse influences of the iodine disinfectant, and the disinfectant is detoxyfied after the contact lens has been disinfected, to thereby avoid coloring of the contact lens while assuring an excellent cleaning effect to remove deposits such as eye lipid adhering to the contact lens.

The above object of the present invention may be attained according to a first aspect of the invention, which provides a method of cleaning and disinfecting a contact lens, comprising the steps of: preparing a disinfectant which is an aqueous solution containing an iodine-complex polymer, and a diluent which is an aqueous solution containing ethylenediamine tetraacetic acid and/or soluble salts thereof, and a nonionic surface active agent; mixing the disinfectant and the diluent to provide a mixed solution, such that an available iodine concentration of the mixed solution immediately after mixing is in a range of 0.01–50 ppm, and such that concentrations of the ethylenediamine tetraacetic acid and/or the soluble salts thereof, and the nonionic surface active agent in the mixed solution are in a range of 0.0001–1.0 w/v % and in a range of 0.01–1.0 w/v %, respectively; and immersing the contact lens in the mixed solution for cleaning and disinfecting the contact lens, the available iodine which remains in the mixed solution being gradually reduced by the ethylenediamine tetraacetic acid and/or the soluble salts thereof.

The above object of the invention may also be attained according to a second aspect of the invention, which provides a method of cleaning and disinfecting a contact lens, comprising the steps of: preparing a disinfectant which is an aqueous solution containing an iodine-complex polymer, and a diluent which is an aqueous solution containing ethylenediamine tetraacetic acid and/or soluble salts thereof, and a nonionic surface active agent; immersing the contact lens in the diluent; and mixing the disinfectant and the diluent in which the contact lens is immersed, such that an available iodine concentration of a mixed solution of the diluent and the disinfectant immediately after mixing is in a range of 0.01–50 ppm, and such that concentrations of the ethylenediamine tetraacetic acid and/or the soluble salts thereof, and the nonionic surface active agent in the mixed solution are in a range of 0.0001–1.0 w/v % and in a range of 0.01–1.0 w/v %, respectively, the available iodine which remains in the mixed solution being gradually reduced by the ethylenediamine tetraacetic acid and/or the soluble salts thereof.

In the contact lens cleaning and disinfecting method according to the present invention, the contact lens is first immersed in the diluent containing the ethylenediamine tetraacetic acid (hereinafter referred to as "EDTA") and/or the soluble salts thereof, and the nonionic surface active agent. To the diluent in which the contact lens is immersed, the disinfectant containing the iodine-complex polymer as the iodine disinfectant is added for cleaning and disinfecting the contact lens. Alternatively, the diluent and the disinfectant are mixed together, so that the available iodine concentration of the mixed solution of the disinfectant and the diluent is lowered prior to immersion of the contact lens therein. Then, the contact lens is immersed in the mixed solution for cleaning and disinfection. In the present method, the nonionic surface active agent has a function of retarding or delaying the reduction of the iodine molecules by the EDTA and/or its soluble salts, in other words, lowering a rate of reduction of the iodine molecules by the EDTA and/or its soluble salts, thereby permitting the available iodine to sufficiently clean and disinfect the contact lens without giving an adverse influence on the contact lens. Further, after the contact lens has been sufficiently disinfected, the reduction of the iodine molecules by the EDTA, which reduction was retarded by the nonionic surface active agent gradually takes places, so that the disinfected contact lens is effectively protected from being colored due to the iodine. Accordingly, the contact lens cleaning and disinfecting method according to the present invention does not require the conventionally used reducing agent such as the sulfur-containing reducing agent.

In a first preferred form of the above first and second aspects of the present invention, the available iodine remaining in the mixed solution is reduced by the EDTA and/or the soluble salts thereof under an effect of light, so that the available iodine can be advantageously reduced.

In a second preferred form of the above first and second aspects of the present invention, the disinfectant contains at least one halogenated compound of alkali metal for stabilizing the available iodine in the disinfectant. According to this arrangement, the iodine molecules in the disinfectant can be effectively stabilized.

In a third preferred form of the above first and second aspects of the present invention, the nonionic surface active agent comprises polyoxyethylene hydrogenated castor oil.

DETAILED DESCRIPTION OF THE PREFERRED EMBODIMENT

In the present contact lens cleaning and disinfecting method, an aqueous solution of an iodine-associated or iodine-complex polymer is used as a disinfectant. The iodine-complex polymer which is an essential component of the disinfectant is known as an iodine germicide or disinfectant. The iodine-complex polymer is also called as iodophor. Unlike a conventional disinfectant containing free iodine, the iodine-complex polymer contains the iodine molecules ($I_2$) which are included in or associated with macromolecules such as polyvinyl pyrrolidone and polyvinyl alcohol. Examples of such an iodine-complex polymer include poly[(2-oxo-1-pyrrolidinyl)ethylene]iodine (known as povidone-iodine), polyvinylalcohol-iodine, polyvinylpyrrolidone-iodine, nonylphenolethoxylate-iodine, soluble starch-iodine, betacyclodextrin-iodine, polyoxyethylene-polyoxypropylene condensate-iodine, and ethoxylated linear alcohol-iodine. In the present invention, the iodine-complex polymer is dissolved in water with a concentration of generally in a range of 0.1–5 w/v %, so as to provide the desired disinfectant. The disinfectant, i.e., the aqueous solution of the iodine-complex polymer contains as a stabilizing agent, a halogenated compound of alkali metal such as sodium chloride or potassium iodide for the purpose of stabilizing the iodine molecules (the effective or available iodine) in the solution. The amount of the halogenated compound is generally in a range of 0.01–20 w/v %.

The diluent which is used in combination with the disinfectant described above for cleaning and disinfecting the contact lens contains at least ethylenediamine tetraacetic acid (EDTA) and/or soluble salts thereof, and a nonionic surface active agent. The diluent and the disinfectant are mixed together for cleaning and disinfecting the contact lens.

The EDTA and/or the soluble salts thereof contained in the diluent functions or function as a chelating agent as known in the art, to prevent calcium salts derived from calcium ions in the tear, from adhering to the contact lens. At the same time, the EDTA and/or its soluble salts reduces or reduce the iodine molecules ($I_2$, $I_3^-$) introduced from the iodine-complex polymer, into the mixed solution, so as to convert $I_2$ to $2I^-$, and $I_3^-$ to $3I^-$. Accordingly, the iodine color of the mixed solution disappears, namely, the iodine in the mixed solution is dissipated. In addition, the EDTA and/or its soluble salts exhibits or exhibit bacteriostatic action (bacteria growth inhibitory effect). Only one of the EDTA and its soluble salts may be used, or the EDTA and its soluble salts may be used in combination. Examples of the soluble salts of the EDTA include a disodium salt, a trisodium salt, and a tetrasodium salt of the EDTA.

The concentration of the EDTA and/or its soluble salts in the diluent is suitably determined such that the EDTA and/or its soluble salts has a concentration in a range of 0.0001–1.0 w/v % in the mixed solution of the diluent and the disinfectant.

The nonionic surface active agent contained in the diluent is effective to improve the cleaning effect with respect to the lipid deposits adhering to the contact lens. In addition, the nonionic surface active agent has a function of lowering the rate of reduction of the iodine molecules ($I_2$, $I_3^-$) by the EDTA and/or its soluble salts. Examples of the nonionic surface active agents include polyoxyethylene castor oil, polyoxyethylene hardened or hydrogenated castor oil, polyoxyethylene sorbitan fatty acid ester, polyoxyethylene alkyl ether, polyoxyethylene stearate, and polyoxyethylene-polyoxypropylene block copolymer. In the present invention, the polyoxyethylene hydrogenated castor oil is preferably used as the nonionic surface active agent. Typical examples of the polyoxyethylene hydrogenated castor oil are polyoxyethylene(40) hydrogenated castor oil, polyoxyethylene(50) hydrogenated castor oil, polyoxyethylene(60) hydrogenated castor oil, polyoxyethylene(80) hydrogenated castor oil, and polyoxyethylene(100) hydrogenated castor oil.

The concentration of the nonionic surface active agent in the diluent is suitably determined such that the nonionic surface active agent has a concentration in a range of 0.01–1.0 w/v % in the mixed solution of the diluent and the disinfectant.

The diluent used in the present invention containing the EDTA and/or its soluble salts and the nonionic surface active agent may further contain suitable additives which have been conventionally used in cleaning and disinfecting the contact lens, such as a buffer and a tonicity adjusting agent. The buffer such as a borate buffer or a phosphate buffer is added to the diluent for the purpose of stabilizing the pH of the mixed solution of the diluent and the disinfectant. The buffer is included in the diluent such that its concentration in the mixed solution is held in a range of 0.05–3.0 w/v %, preferably in a range of 0.1–1.5 w/v %. If the concentration of the buffer in the mixed solution is lower than 0.05 w/v %, it is difficult to keep the pH of the mixed solution at a desired level. On the other hand, the concentration of the buffer in the mixed solution exceeding 3.0 w/v % does not significantly improve the effect of stabilizing the pH of the mixed solution. Owing to the inclusion of the buffer in the diluent, the pH of the mixed solution is kept in a range of 6.0–8.0. The pH of the mixed solution held in the above range does not cause any troubles with the eyes. The tonicity adjusting agent is used to mitigate irritation to the eyes. The tonicity adjusting agent known in the art such as sodium chloride, potassium chloride, glycerin or propylene glycol is included in the diluent such that the osmotic pressure of the mixed solution is held generally in a range of 150–400 mOsm, preferably in a range of 200–350 mOsm.

In cleaning and disinfecting a contact lens by using the disinfectant and the diluent prepared as described above, the diluent and the disinfectant are mixed together to provide a mixed solution, and the contact lens is immersed in the mixed solution immediately after mixing. Alternatively, the contact lens is first immersed in the diluent, and the disinfectant is added to the diluent in which the contact lens is immersed. In this case, the contact lens is brought into contact with the disinfectant while it is immersed in the diluent, so that the contact lens is prevented from being colored by the iodine in the disinfectant. Further, in the present method wherein the reduction of the iodine molecules by the EDTA and/or its soluble salts is delayed or retarded by the nonionic surface active agent, the contact lens can be sufficiently and effectively cleaned and disinfected owing to the iodine introduced from the disinfectant into the mixed solution. In contrast, where the diluent does not include the nonionic surface active agent, the iodine molecules in the disinfectant are reduced by the EDTA and/or its soluble salts immediately after the disinfectant is mixed with the diluent. In this case, the contact lens cannot be sufficiently disinfected by the iodine.

The diluent and the disinfectant are mixed together to provide the mixed solution, such that the available iodine concentration of the mixed solution is held in a range of 0.01–50 ppm, and such that the concentrations of the EDTA and/or its soluble salts, and the nonionic surface active agent of the mixed solution are held in a range of 0.0001–1.0 w/v % and in a range of 0.01–1.0 w/v %, respectively.

The concentration of the available iodine in the mixed solution immediately after mixing of the diluent and the disinfectant needs to be 0.01 ppm or higher for providing a sufficiently high disinfecting effect. If the available iodine concentration exceeds 50 ppm, the iodine cannot be adequately reduced by the EDTA and/or its soluble salts, so that the contact lens may be undesirably colored by the iodine after it has been disinfected. The available iodine concentration of the mixed solution is held preferably in a range of 0.1–40 ppm, more preferably 1–30 ppm.

The EDTA and/or its soluble salts are used in an amount such that the concentration of the EDTA and/or its soluble salts in the mixed solution is held generally in a range of 0.0001–1.0 w/v %, preferably in a range of 0.001–0.5 w/v %, more preferably in a range of 0.001–0.1 w/v %. If the concentration of the EDTA and/or its soluble salts in the mixed solution is lower than 0.001 w/v %, the iodine molecules existing in the mixed solution cannot be sufficiently reduced. In this case, the contact lens which has been cleaned and disinfected tends to be colored by the iodine. On the other hand, if the concentration of the EDTA and/or its soluble salts exceeds 1.0 w/v %, the iodine molecules are reduced faster than desired, lowering the disinfecting effect to be exhibited by the iodine.

The nonionic surface active agent is used in an amount such that its concentration in the mixed solution is held generally in a range of 0.01–1.0 w/v %, preferably in a range of 0.02–0.8 w/v %, more preferably in a range of 0.05–0.5 w/v %. The concentration of the nonionic surface active agent in the mixed solution lower than 0.01 w/v % is not effective to slow the reduction of the iodine molecules by the EDTA and/or its soluble salts to a desired extent. In this case, the iodine is reduced faster than desired, resulting in insufficient disinfection of the contact lens and a lowered stain removal effect for removing lipid deposits adhering to the contact lens. On the other hand, the concentration of the nonionic surface active agent exceeding 1.0 w/v % means that the nonionic surface active agent is used beyond an amount suitable for cleaning the contact lens. The use of an excessively large amount of the nonionic surface active agent is not economical, and results in deterioration of the disinfecting effect to be exhibited by the iodine.

According to the present contact lens cleaning and disinfecting method, the contact lens is immersed in the mixed solution of the disinfectant and the diluent, or the contact lens is initially immersed in the diluent and then the disinfectant is added to the diluent in which the lens has been immersed. The contact lens is held in contact with the mixed solution of the disinfectant and the diluent for a suitable time period, generally for a time period from several minutes to four hours, preferably for a time period from several minutes to one hour, whereby the contact lens can be effectively cleaned and disinfected. In the present invention, it is desirable that the contact lens be cleaned and disinfected under an effect of light, so that the iodine can be effectively reduced by the EDTA and/or its soluble salts.

For cleaning and disinfecting the contact lens under an effect of light, a suitable container which permits transmission of light such as ordinary indoor light is used for accommodating the contact lens. When such a container consists of a main body and a lid like contact lens cases generally used in cleaning and disinfecting the contact lens, the main body of the container is formed of a suitable transparent material which permits the transmission of light. In cleaning and disinfecting the contact lens by using the container described above, the contact lens is accommodated in the main body of the container, and the container is filled with the mixed solution of the diluent and the disinfectant. In this state, the contact lens is effectively cleaned and disinfected under an effect of light.

The above-described transparent container for accommodating the contact lens permits the transmission of ordinary indoor light. Preferably, the container permits the transmission of not smaller than 40% of a light having a wavelength of 350–900 nm, more preferably not smaller than 60% of the light. The contact lens is accommodated in the container described above and held in contact with the mixed solution of the disinfectant and the diluent, so that the contact lens is cleaned and disinfected. In the present arrangement, the iodine introduced from the disinfectant into the mixed solution is gradually reduced by the EDTA and/or its soluble salts in the presence of the nonionic surface active agent under an effect of light, whereby the iodine in the mixed solution is dissipated. Accordingly, the contact lens can be disinfected to a satisfactory extent without being colored by the iodine which would be otherwise adsorbed in the contact lens after the contact lens has been cleaned and disinfected. If the container for accommodating the contact lens has a low light transmission property, the iodine in the mixed solution cannot be sufficiently reduced.

The above-described container for accommodating the contact lens used for cleaning and disinfecting the lens is formed of any transparent material such as a glass. Preferably, the container is formed of widely-used plastics such as polycarbonate, polymethyl methacrylate, polyethylene, polypropylene, and polystyrene, which are relatively inexpensive and exhibit a relatively high mechanical strength. Although the configuration of the transparent container is not particularly limited, the transparent container is desirably shaped such that at least a portion of its upper wall and/or side wall is formed of a light-transparent material.

In the present contact lens cleaning and disinfecting method as described above, the conventionally used protease in a liquid, solid or powdered form may be added to the diluent or the disinfectant in an attempt to remove protein deposits adhering to the contact lens.

EXAMPLES

To further clarify the concept of the present invention, some examples of the invention will be described. It is to be understood that the invention is not limited to the details of the illustrated examples, but may be embodied with various changes, modifications and improvements, which may occur to those skilled in the art without departing from the scope of the invention as defined in the attached claims.

Example 1

Initially, there were prepared two disinfectants No.1 and No. 2 in the following manner.

[Disinfectant No. 1]

2.16 g of a commercially available povidone-iodine powder (available from BASF CORPORATION, USA) as an iodine-complex polymer was dissolved in 500 ml of purified water, to thereby provide the disinfectant No.1 whose available iodine concentration is 500 ppm.

[Disinfectant No. 2]

2.16 g of the above povidone-iodine and 12.5 g of sodium chloride (available from WAKO JUNYAKU KOGYO, K.K., Japan) were dissolved in purified water, to thereby provide the disinfectant No. 2 whose available iodine concentration and the concentration of the sodium chloride are 500 ppm and 2.5 w/v %, respectively.

Next, there were prepared six diluents Nos. 1–6 by using the following nonionic surface active agents: HCO-60 which is polyoxyethylene(60) hydrogenated castor oil and available from NIKKO CHEMICALS CO. Ltd., Japan; E-230 which is polyoxyethylene(30) oleylether and available from Nippon Oil & Fats Co., Ltd., Japan; and TO-10M which is polyoxyethylene(20) sorbitan monooleate and available from NIKKO CHEMICALS CO., Ltd., Japan. The diluents Nos. 1–6 were prepared so as to have the respective compositions as indicated in the following Table 1. The diluents Nos. 1–6 included sodium chloride (available from WAKO JUNYAKU KOGYO K.K., Japan), boric acid, borate (both available from NIKKO SEIYAKU CO., Ltd., Japan), and EDTA-2Na (available from TEIKOKU KAGAKU CO., Ltd., Japan), in the respective amounts indicated in the Table 1.

TABLE 1

| | Diluent No. | | | | | |
|---|---|---|---|---|---|---|
| | 1 | 2 | 3 | 4 | 5 | 6 |
| sodium chloride | 0.72 | 0.72 | 0.72 | 0.72 | 0.72 | 0.72 |
| boric acid | 0.39 | 0.39 | 0.39 | 0.39 | 0.39 | 0.39 |
| borate | 0.03 | 0.03 | 0.03 | 0.03 | 0.043 | 0.03 |
| EDTA.2Na | 0.1 | 0.1 | 0.1 | 0.1 | 0.1 | 0.1 |
| HCO-60 | 0.2 | — | — | 0.1 | 0.1 | — |
| E-230 | — | 0.2 | — | — | — | — |
| TO-10M | — | — | 0.2 | — | — | — |

(unit: w/v %)

The thus prepared disinfectants Nos. 1 and 2, and the diluents Nos. 1–6 were mixed in test tubes made of glass, in combinations as indicated in the following Tables 2 and 3, so that various treating solutions (mixed solutions) were prepared such that 10 ml of the treating solutions had different values of the initial available iodine concentration as indicated in the Tables 2 and 3. After mixing the disinfectants and the diluents to provide the treating solutions, a time period required before the color of the iodine has disappeared was measured for each of the treating solutions. The results of the measurement are also indicated in the Tables 2 and 3.

TABLE 2

| | Treating solution No. | | | | | | | |
|---|---|---|---|---|---|---|---|---|
| | 1 | 2 | 3 | 4 | 5 | 6 | 7 | 8 |
| Disinfectant No. | 1 | 1 | 1 | 1 | 1 | 1 | 1 | 1 |
| Diluent No. | 1 | 1 | 2 | 2 | 2 | 3 | 4 | 5 |
| available iodine concentration (ppm) | 20 | 10 | 25 | 20 | 10 | 10 | 12.5 | 12.5 |
| required time before the iodine color disappears (seconds) | 180 | 120 | 270 | 200 | 150 | 270 | 150 | 150 |

TABLE 3

| | Treating solution No. | | | | | | |
|---|---|---|---|---|---|---|---|
| | 9 | 10 | 11 | 12 | 13 | 14 | 15 |
| Disinfectant No. | 1 | 1 | 1 | 1 | 1 | 1 | 2 |
| Diluent No. | 6 | 6 | 6 | 6 | 6 | 6 | 6 |
| available iodine concentration (ppm) | 10 | 20 | 30 | 40 | 50 | 60 | 50 |
| required time before the iodine color disappears (seconds) | $\leq 10$ | $\leq 10$ | $\leq 10$ | $\leq 10$ | $\leq 10$ | 120 | $\leq 10$ |

As is apparent from the results indicated in the Tables 2 and 3, in the treating solutions Nos. 1–8 which used the diluents Nos. 1–5 containing the nonionic surface active agents according to the present invention, the color of the iodine disappeared some time after the mixing of the diluent and disinfectant. That is, the iodine was gradually reduced by the EDTA·2Na. Accordingly, it was observed that the treating solutions Nos. 1–8 exhibited satisfactory disinfecting effect attained by the iodine. In contrast, in the treating solutions Nos. 9–15 (as comparative examples) which used the diluents No. 6 without containing the nonionic surface active agent, the reduction of the iodine by the EDTA·2Na was initiated immediately after the mixing of the diluent and the disinfectant, so that the color of the iodine disappeared in a considerably short period of time, in other words, the iodine was reduced faster than desired. Accordingly, the treating solutions Nos. 9–15 did not exhibit a sufficient disinfecting effect owing to the iodine.

Example 2

The treating solutions Nos.1–6 (according to the present invention) and Nos. 9–13 (as the comparative examples) as used in the above Example 1 were evaluated of the sterilizing and disinfecting effect with respect to the fungi in the following manner. Namely, as the test fungi, C. a. (*Candida albicans* ATCC 10231) and F. s. (*Fusarium solani* ATCC 36031) were inoculated into respective specimens of the diluents (Nos. 1–3 and No. 6) of the treating solutions Nos. 1–6 and Nos. 9–13, in initial fungi amounts of $7 \times 10^6$ cfu/ml and $2.7 \times 10^5$ cfu/ml, respectively. The disinfectant (No. 1) used in the above Example 1 was mixed with the diluents, and the obtained mixed solutions (treating solutions) were left for ten minutes. Thereafter, the viable cell count was measured for each treating solution by a mixing and dilution method. On the basis of the measured viable cell count, the rate of decrease in the number of the fungi was calculated in logarithm. The results of the calculation are indicated in the following Table 4.

TABLE 4

| Treating solution No. | Log reduction with respect to C. a. | Log reduction with respect to F. s. |
|---|---|---|
| Present Invention | | |
| 1 | 2.2 | >2 |
| 2 | 0.7 | >2 |
| 3 | 1.3 | >2 |
| 4 | 1.0 | >2 |
| 5 | 0.3 | — |
| 6 | 0.1 | — |
| Comparative Examples | | |
| 9 | <0.1 | <0.1 |
| 10 | <0.1 | <0.1 |
| 11 | <0.1 | <0.1 |
| 12 | <0.1 | <0.1 |
| 13 | <0.1 | <0.1 |

It will be understood from the results of the above Table 4 that the treating solutions Nos. 1–6 according to the present invention exhibited high rates of decrease in the number of the fungi, whereas the treating solutions Nos. 9–13 as the comparative examples did not exhibit a satisfactory sterilizing and disinfecting effect since the reduction of the iodine contained therein was completed within a short period of time.

Example 3

In this Example 3, the treating solutions Nos. 2 and 4 as used in the above Example 1 were evaluated of the sterilizing and disinfecting effect with respect to the bacteria. As the test bacteria, St. a. (*Staphylococcus aureus* ATCC 6538), S. m. (*Serratia marcescens* ATCC 13880), and P a. (*Pseudomonas aeruginoza* ATCC 9027) were inoculated into respective specimens of the diluents (Nos. 1 and 2) of the treating solutions Nos. 2 and 4, in amounts of $5.6 \times 10^5$ cfu/ml, $2.9 \times 10^5$ cfu/ml, and $1.0 \times 10^6$ cfu/ml, respectively. The rate of decrease in the number of the bacteria was calculated for each of the treating solutions Nos. 2 and 4, in a manner similar to that in the Example 2. The results are indicated in the following Table 5. As is apparent from the results of the Table 5, the treating solutions Nos. 2 and 4 exhibited an excellent sterilizing and disinfecting effect.

TABLE 5

| Treating solution No. | test bacteria | | |
|---|---|---|---|
| | St. a. | S. m. | P. a. |
| 2 | >4 | 2.6 | >5 |
| 4 | >4 | 3.2 | >5 |

Example 4

In this Example 4, the treating solutions Nos. 7 and 8 as used in the above Example 1 were evaluated of the disinfecting effect. As the test bacteria, the C. a. was inoculated into respective specimens of the diluents (Nos. 4 and 5) of the treating solutions Nos. 7 and 8, in an amount of $1.2 \times 10^5$ cfu/ml. The rate of decrease in the number of the bacteria was calculated for each of the treating solutions Nos. 7 and 8, in a manner similar to that in the Example 2, except that the treating solution No. 7 was accommodated in a transparent plastic container made of polystyrene in place of the glass tube, and except that the treating solution No. 7 was examined of its disinfecting effect under indoor light. The treating solutions Nos. 7 and 8 exhibited the bacteria decrease rates of not lower than 3 Log.

Example 5

As in the above Example 1, a treating solution was prepared by mixing the disinfectant No. 2 and the diluent No. 4. The prepared treating solution was accommodated in a transparent plastic container (made of polystyrene) which permits the transmission of light therethrough. The treating solution was accommodated in another plastic container which shields the light. The time period required before the color of the iodine has disappeared was measured for the treating solution in the light-transparent container and in the light-shielding container. The results are shown in the following Table 6.

TABLE 6

| | Container | |
| --- | --- | --- |
| | light-transparent container | light-shielding container |
| Disinfectant No. | 2 | 2 |
| Diluent No. | 4 | 4 |
| available iodine concentration (ppm) | 12.5 | 12.5 |
| required time before the iodine color disappears (seconds) | 150 | 300 |

As is apparent from the results of the Table 6, in the treating solution accommodated in the light-transparent container wherein the reduction of the iodine took place under an effect of light, the iodine color has disappeared in a shorter period of time than in the treating solution accommodated in the light-shielding container. Accordingly, it was recognized that the treating solution is capable of preventing the coloring of the contact lens when the reduction of the iodine takes place under an effect of light. A similar experiment was effected by first immersing the contact lenses in the diluent and then adding the disinfectant to the diluent. The experiment revealed that the contact lenses were prevented from being colored by the iodine in both cases using the light-transparent and the light-shielding containers, respectively.

Example 6

Initially, an artificial tear fluid was prepared, which contains 0.388 w/v % of albumin, 0.161 w/v % of γ-globulin, 0.120 w/v % of lysozyme, 0.9 w/v % of sodium chloride, 0.015 w/v % of calcium chloride dihydrate, and 0.104 w/v % of sodium dihydrogenphosphate dihydrate. The pH of the artificial tear fluid was adjusted to 7.0.

The following experiment was conducted on two kinds of water-content soft contact lenses, i.e., "SOFT MA" and "SOFT 72" (both available from Menicon Co., Ltd., Japan). The soft contact lenses were respectively immersed at 40° C. for one hour in 2 ml of the artificial tear solution prepared as described above. Thereafter, each of the lenses was lightly finger-rubbed by using the diluent No. 2. The lens was accommodated in a transparent plastic container filled with 2 ml of the treating solution No. 4, and left for ten minutes. These steps were repeated 30 times ("first cycling test"). Similar steps were repeated 30 times on the two kinds of soft contact lenses ("second cycling test"), except that the diluent No. 4 was used in place of the diluent No. 2, and except that the treating solution No. 7 was used in place of the treating solution No. 4.

In both cycling tests, the contact lenses did not suffer from any troubles such as changes in the color and the size.

Example 7

By using the soft contact lenses which were subjected to the second cycling test described in the above Example 6, the following experiment according to the agar layer method was conducted in a manner described below.

1) L-929 cells were lysed, and poured into a tissue culture flask together with a medium. The mixture was cultured in a $CO_2$ incubator at 37° C. under 5% $CO_2$ and saturated vapor.

2) The surfaces of the cells were washed with 15 ml of PBS(−). After 6 ml of a trypsin-EDTA solution was spread over the surfaces of the cells, the solution was removed therefrom. Two or three minutes later, the cells were observed by a microscope. When the microscope observation revealed that the cells were rounded, the cells were peeled off from the surfaces of the flask by tapping the flask. Immediately after the cells were peeled off, a new medium was added to the cells, and the activity of trypsin ceased. The cells were broken into pieces by lightly pipetting them. Then, the number of the cells was measured by a Bürker-Türk counting chamber (hemocytometer), and the cells were diluted with the medium so as to provide a cell suspension containing the cells in an amount of $2.0 \times 10^5$ cell/ml.

3) 4.5 ml of the thus prepared cell suspension was inoculated in a Petri dish of 60 mm×15 mm (available from FALCON, U.S.A., for tissue culture), and was cultured in the $CO_2$ incubator for 48 hours.

4) To the cultured cell suspension in the Petri dish, 4.5 ml of agar medium was poured. After the agar medium was hardened, 4.5 ml of of 0.01% Neutral red·PBS(−) solution was added, and the cell suspension was cultured in the $CO_2$ incubator for two hours. The contact lens which has been rinsed by rubbing for ten seconds was subjected to a cutting operation wherein the contact lens was cut at its four peripheral portions which are equiangularly spaced from each other in the circumferential direction, and was placed horizontally on the Agar medium in the Petri dish.

5) In this state, the cell suspension was cultured at 37° C. for 24 hours.

The cultured cell suspension in which the cells were stained in red was examined of the degree of staining of the cells around and below the contact lens, by disposing the Petri dish in a white background. It was confirmed that the cell suspension did not suffer from undesirable decrease in the degree of staining of the cells.

Example 8

A soft contact lens "SOFT MA" (available from Menicon Co., Ltd., Japan) was immersed, and boiled in the artificial tear fluid prepared in the above Example 6, whereby the soft contact lens was stained with artificial protein deposits. After the protein deposits were observed by a stereoscopic microscope, the soft contact lens stained with the protein deposits was cut into four pieces. Three of the four pieces were used as test pieces Nos. 1–3 in the following experiment.

In this experiment, the test pieces Nos. 1 and 2 were treated by the treating solution No. 7 prepared in the above Example 1, which contained the diluent No. 4 and the disinfectant No. 2. The test piece No. 1 was accommodated in a transparent plastic container which was filled with the diluent No. 4. The disinfectant No. 2 was added to the diluent No. 4 in which the test piece No. 1 had been immersed, so that the mixed solution (i.e., the treating solution No. 7) had a total volume of 2 ml. The test piece No. 2 was accommodated in a transparent plastic container which was filled with the diluent No. 4, to which one drop (0.03 ml) of a liquid protease derived from Bacillus was added. The disinfectant No. 2 was added to the mixture of the diluent No. 4 and the liquid protease in which the test piece No. 2 had been immersed, so that the mixed solution had a total volume of 2 ml. The test piece No. 3 was accommodated in a transparent plastic container which was filled with 2 ml of a commercially available contact lens cleaning agent ("CLEAN BOTTLE SOAK" available from Menicon Co., Ltd., Japan), to which one drop of the above-described liquid protease was added. The test pieces Nos. 1–3 accommodated in the respective containers were left for two hours.

Each of the test pieces Nos. 1–3 was observed by the stereoscopic microscope. The observation revealed that the protein deposits remained on the test piece No. 1 whereas they were removed from the test pieces Nos. 2 and 3. In view of the result that the protein deposits were removed from the test piece No. 3 which had been immersed in the mixture of the treating solution No.7 and the liquid protease, it was confirmed that the enzyme activity of the liquid protease was not inhibited by the treating solution 7, whereby the protein deposits on the test piece No. 3 were removed by the liquid protease.

Example 9

For each of the treating solution No. 7 used in immersing the test piece No. 1, and the mixture of the treating solution No. 7 and the liquid protease used in immersing the test piece No. 2 in the above Example 8, the bacteria decrease rate was calculated by using $3.7 \times 10^5$ cfu/ml of $S.\ m.$, in a manner similar to that in the above Example 3. The bacteria decrease rate was 2 Log in both of the two solutions. Accordingly, it was found that the liquid enzyme (protease) did not inhibit the disinfecting effect exhibited by the treating solution No. 7.

Example 10

As an oxygen permeable hard contact lens, "MENICON EX" and "MENICON SUPER EX" (both available from Menicon Co., Ltd., Japan) were prepared. Each hard contact lens was accommodated in a transparent container together with the diluent No. 4 prepared in the above Example 1. Then, the disinfectant No. 2 was mixed with the diluent in which the hard contact lens had been immersed, in an amount such that the available iodine concentration of the mixed solution was 12.5 ppm. In this state, the mixture was left for ten minutes. This experiment was repeated 30 times. After the 30-times experiment, it was confirmed that the contact lens did not suffer from any changes in its color and base curve.

What is claimed is:

1. A method of cleaning and disinfecting a contact lens, comprising the steps of:

preparing a disinfectant which is an aqueous solution containing polyvinylpyrrolidone-iodine, and a diluent which is an aqueous solution containing ethylenediamine tetraacetic acid and/or soluble salts thereof, and a nonionic surface active agent selected from the group consisting of polyoxyethylene castor oil, polyoxyethylene hardened or hydrogenated castor oil, polyoxyethylene sorbitan fatty acid ester, polyoxyethylene alkyl ether, polyoxyethylene stearate, polyoxyethylene-polyoxypropylene block copolymer and mixtures thereof;

immersing said contact lens in said diluent; and mixing said disinfectant and said diluent in which said contact lens is immersed, such that an available iodine concentration of a mixed solution of said diluent and said disinfectant immediately after mixing is in a range of 0.01–50 ppm, and such that concentrations of said ethylenediamine tetraacetic acid and/or said soluble salts thereof, and said nonionic surface active agent in said mixed solution are in a range of 0.0001–1.0 w/v % and in a range of 0.01–1.0 w/v %, respectively, said nonionic surface active agent lowering a rate of reduction of said available iodine in said mixed solution, so that said available iodine which remains in said mixed solution is gradually reduced by said ethylenediamine tetraacetic acid and/or said soluble salts thereof.

2. A method according to claim 1, wherein said available iodine remaining in said mixed solution is reduced by said ethylenediamine tetraacetic acid and/or said soluble salts thereof under an effect of light.

3. A method according to claim 1, wherein said disinfectant contains at least one halogenated compound of alkali metal for stabilizing said available iodide in said disinfectant.

4. A method according to claim 3, wherein said at least one halogenated compound of alkali metal is contained in said disinfectant in an amount of 0.01–20 w/v %.

5. A method according to claim 1, wherein said nonionic surface active agent comprises polyoxyethylene hydrogenated castor oil.

6. A method according to claim 1, wherein said soluble salts of said ethylenediamine tetraacetic acid comprise a disodium salt, a trisodium salt and a tetrasodium salt of said ethylenediamine tetraacetic acid.

7. A method of cleaning and disinfecting a contact lens, comprising the steps:

preparing a disinfectant which is an aqueous solution containing polyvinylpyrrolidone-iodine, and a diluent which is an aqueous solution containing ethylenediamine tetraacetic acid and/or soluble salts thereof, and a nonionic surface active agent selected from the group consisting of polyoxyethylene castor oil, polyoxyethylene hardened or hydrogenated castor oil, polyoxyethylene sorbitan fatty acid ester, polyoxyethylene alkyl ether, polyoxyethylene stearate, polyoxyethylene-polyoxypropylene block copolymer and mixtures thereof;

cleaning and rinsing said contact lens with said diluent;

immersing said contact lens in said diluent; and mixing said disinfectant and said diluent in which said contact lens is immersed, such that an available iodine concentration of a mixed solution of said diluent and said disinfectant immediately after mixing is in a range of 0.01–50 ppm, and such that concentrations of said ethylenediamine tetraacetic acid and/or said soluble salts thereof, and said nonionic surface active agent in said mixed solution are in a range of 0.0001–1.0 w/v % and in a range of 0.01–1.0 w/v %, respectively, said nonionic surface active agent lowering a rate of reduction of said available iodine in said mixed solution, so that said available iodine which remains in said mixed solution is gradually reduced by said ethylenediamine tetraacetic acid and/or said soluble salts thereof.

8. A method of lowering a rate of reduction of an available iodine in a mixed solution used for cleaning and disinfecting a contact lens, said mixed solution consisting of a disinfectant which is an aqueous solution containing polyvinylpyrrolidone-iodine and a diluent which is an aqueous solution containing ethylenediamine tetraacetic acid and/or soluble salts thereof, said method comprising including, in said diluent, a nonionic surface active agent selected from the group consisting of polyoxyethylene castor oil polyoxyethylene hardened or hydrogenated castor oil, polyoxyethylene sorbitan fatty acid ester, polyoxyethylene alkyl ether, polyoxyethylene stearate, polyoxyethylene-polyoxypropylene block copolymer and mixtures thereof, wherein an available iodine concentration in said mixed solution is in a range of 0.01–50 ppm, and concentrations of said ethylenediamine tetraacetic acid and/or said soluble salts thereof, and said nonionic surface active agent in said mixed solution are in a range of 0.0001–1.0 w/v % and in a range of 0.01–1.0 w/v %, respectively.

9. A method of stabilizing an available iodine in a disinfectant which is an aqueous solution containing polyvinylpyrrolidone-iodine and at least one halogenated compound of alkali metal mixed with a diluent for cleaning and disinfecting a contact lens, said diluent being an aqueous solution containing ethylenediamine tetraacetic acid and/or soluble salts thereof, and a nonionic surface active agent selected from the group consisting of polyoxyethylene castor oil, polyoxyethylene hardened or hydrogenated castor oil, polyoxyethylene sorbitan fatty acid ester, polyoxyethylene alkyl ether, polyoxyethylene stearate, polyoxyethylene-polyoxypropylene block copolymer and mixtures thereof, wherein an available iodine concentration in said solution is in a range of 0.01–50 ppm, and concentrations of said ethylenediamine tetraacetic acid and/or said soluble salts thereof, and said nonionic surface active agent in said solution are in a range of 0.0001–1.0 w/v % and in a range of 0.01–1.0 w/v %, respectively.

* * * * *